(12) United States Patent
Mucha et al.

(10) Patent No.: US 11,864,847 B2
(45) Date of Patent: Jan. 9, 2024

(54) SENSOR CARRIER

(71) Applicant: Intersect ENT International GmbH, Hennigsdorf (DE)

(72) Inventors: Dirk Mucha, Glienicke/Nordbahn (DE); Kai Desinger, Berlin (DE); Nicholas Norman, Charlotte, NC (US)

( * ) Notice: Subject to any disclaimer, the term of this patent is extended or adjusted under 35 U.S.C. 154(b) by 0 days.

(21) Appl. No.: 17/516,568

(22) Filed: Nov. 1, 2021

(65) Prior Publication Data
US 2022/0047338 A1 Feb. 17, 2022

Related U.S. Application Data

(63) Continuation of application No. PCT/EP2020/062086, filed on Apr. 30, 2020.
(Continued)

(51) Int. Cl.
*A61B 34/20* (2016.01)
*A61B 5/00* (2006.01)

(52) U.S. Cl.
CPC ............ *A61B 34/20* (2016.02); *A61B 5/6853* (2013.01); *A61B 2034/2053* (2016.02)

(58) Field of Classification Search
CPC .................. A61B 34/20; A61B 5/6853; A61B 2034/2053; A61B 5/6852; A61B 5/062; A61B 2034/2051

See application file for complete search history.

(56) References Cited

U.S. PATENT DOCUMENTS 9,471,850 B2 10/2016 Krueger
10,022,525 B2 7/2018 Hanson
(Continued)

FOREIGN PATENT DOCUMENTS

DE 102011119073 A1 5/2013
EP 0691663 A1 1/1996
(Continued)

OTHER PUBLICATIONS

European Patent Office, International Search Report and Written Opinion for PCT/EP2020/062086, dated Aug. 7, 2020, 10 pages.
(Continued)

*Primary Examiner* — Hien N Nguyen
(74) *Attorney, Agent, or Firm* — Nancy C. Wilker

(57) ABSTRACT

The invention relates to an auxiliary instrument for insertion into vessels or lumens with small inner diameters. The auxiliary instrument has a proximal end and a distal end and has at least one localization element whose position and orientation can be determined with an electromagnetic position detection system. The localization element is located directly adjacent to or at least close to the distal end of the auxiliary instrument and is configured to capture an alternating electromagnetic field. A distal end region of the auxiliary instrument extends from the distal end of the auxiliary instrument to a proximal end of the localization element such that the localization element is located within the distal end region. In that part of the distal end region in which the localization element is located, the auxiliary instrument has a low bending stiffness of less than 10 $Nmm^2$, at least in sections. At least two lines are led from the localization element to the proximal end of the auxiliary instrument and are electrically conductively connected at least to the localization element. The localization element has a length with an amount that is at least ten times the amount of an outer diameter of the localization element.

36 Claims, 6 Drawing Sheets

Related U.S. Application Data

Figure 1:
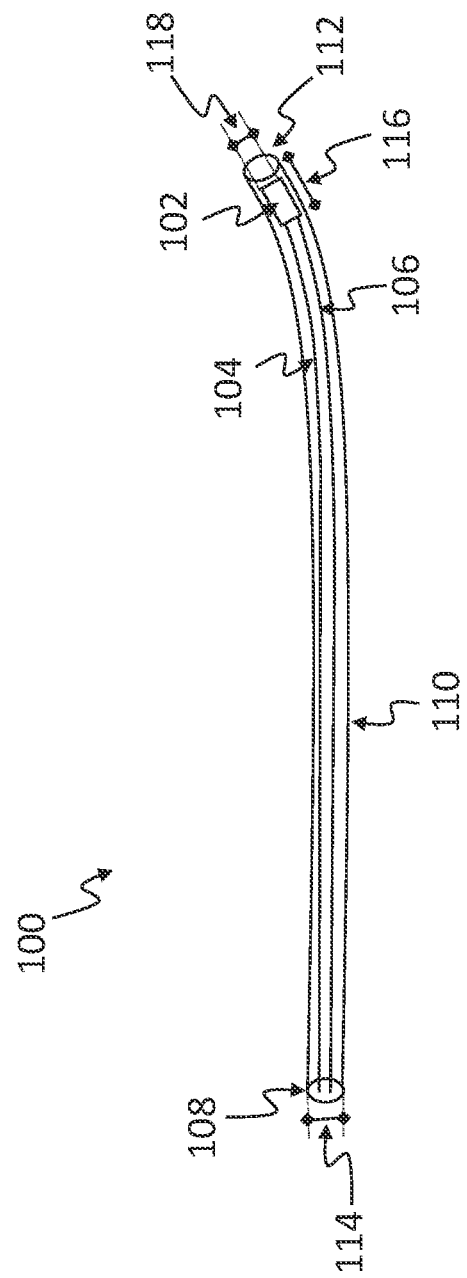

(60) Provisional application No. 62/842,025, filed on May 2, 2019.

(56) References Cited

U.S. PATENT DOCUMENTS

| | | |
|---|---|---|
| 10,238,846 B2 | 3/2019 | Ressemann |
| 2003/0066538 A1 | 4/2003 | Martinelli |
| 2009/0234329 A1 | 9/2009 | Inamoto |
| 2010/0274188 A1 | 10/2010 | Chang |
| 2011/0066029 A1 | 3/2011 | Lyu |
| 2014/0163546 A1* | 6/2014 | Govari ............... A61B 18/1206 606/41 |
| 2014/0303489 A1 | 10/2014 | Meier |
| 2014/0317910 A1 | 10/2014 | Govari |
| 2016/0310041 A1 | 10/2016 | Jenkins |
| 2017/0028112 A1 | 2/2017 | Drontle |
| 2017/0196508 A1 | 7/2017 | Hunter |
| 2018/0093087 A1* | 4/2018 | Beach ............... A61M 25/0069 |
| 2018/0296811 A1 | 10/2018 | Chan |
| 2019/0015644 A1 | 1/2019 | Thomspon Smith |
| 2019/0038366 A1 | 2/2019 | Johnson |

FOREIGN PATENT DOCUMENTS

| | | |
|---|---|---|
| WO | WO 2012150567 A1 | 11/2012 |
| WO | WO2020/221885 A1 | 11/2020 |
| WO | WO2020221940 A1 | 11/2020 |

OTHER PUBLICATIONS

The International Bureau of WIPO, International Preliminary Report on Patentability for PCT/EP2020/062086, dated Nov. 2, 2021, 7 pages.

European Patent Office, International Search Report and Written Opinion for PCT/EP2020/062349, dated Aug. 7, 2020, 13 pages.

The International Bureau of WIPO, International Preliminary Report on Patentability for PCT/EP2020/062349, dated Nov. 2, 2021, 9 pages.

* cited by examiner

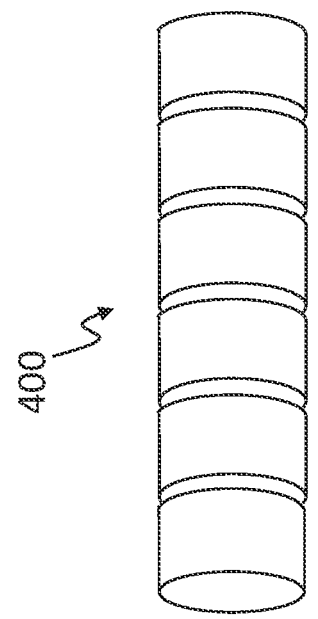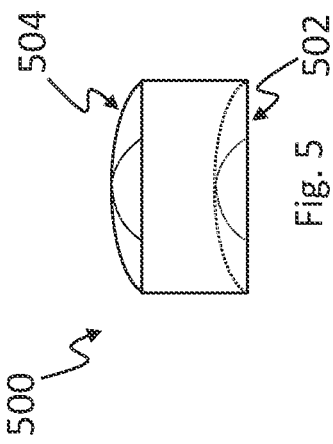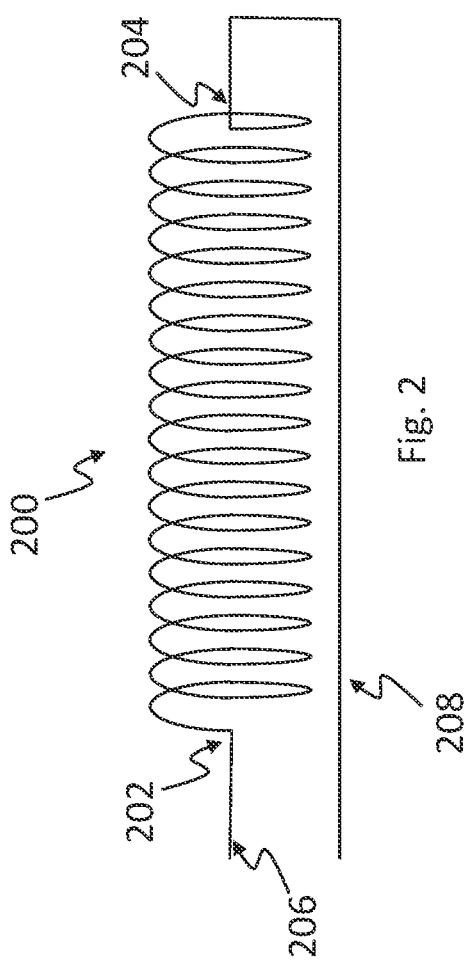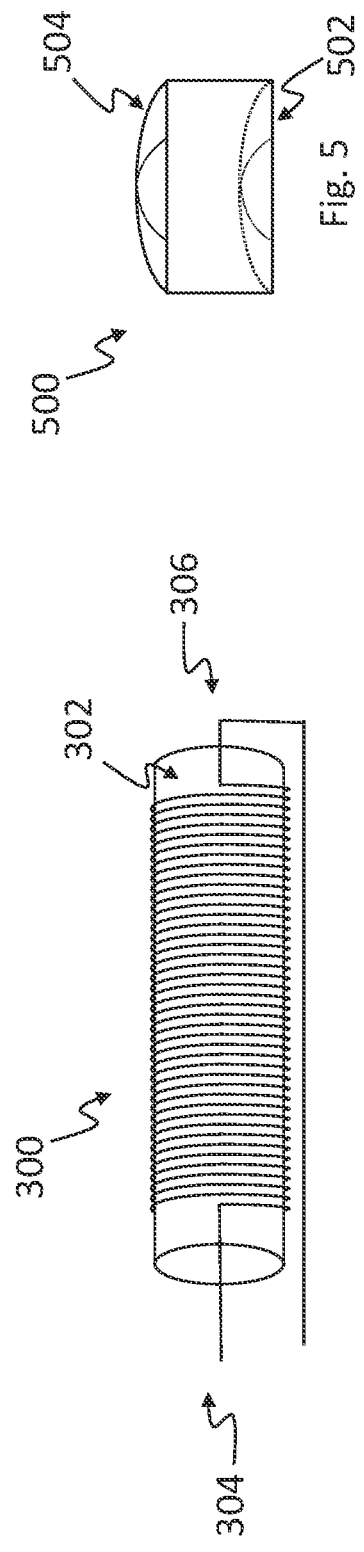

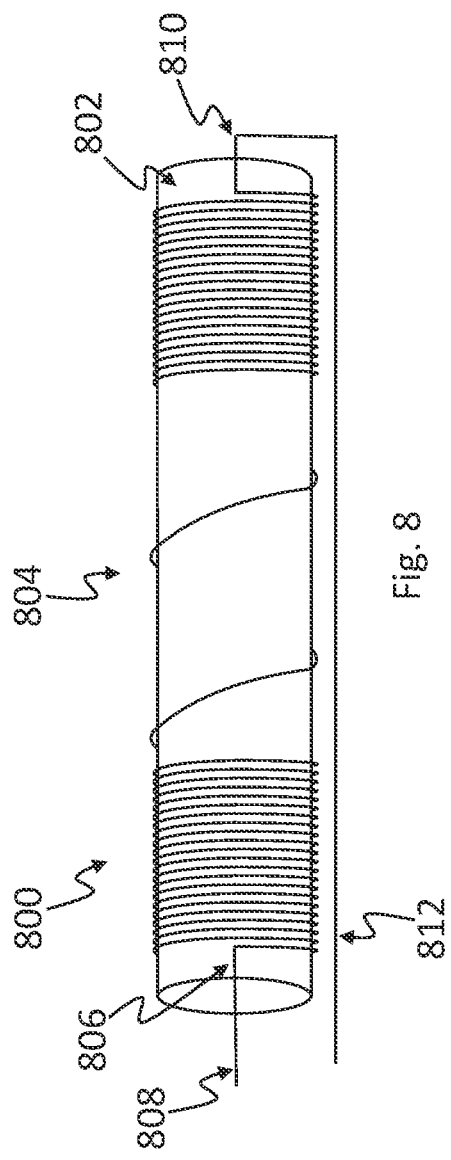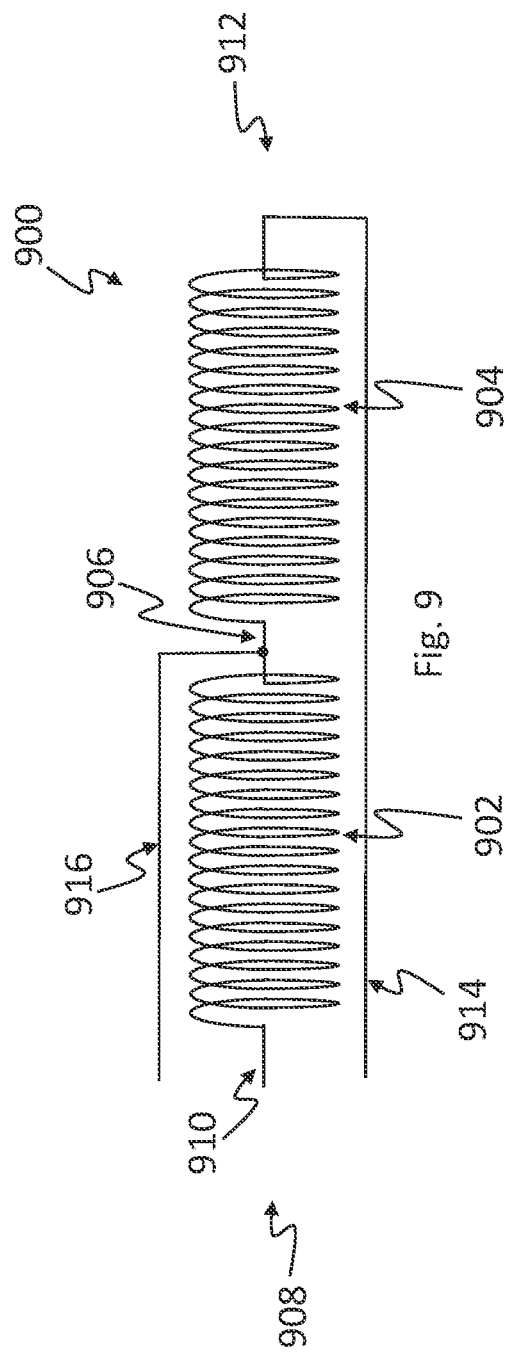

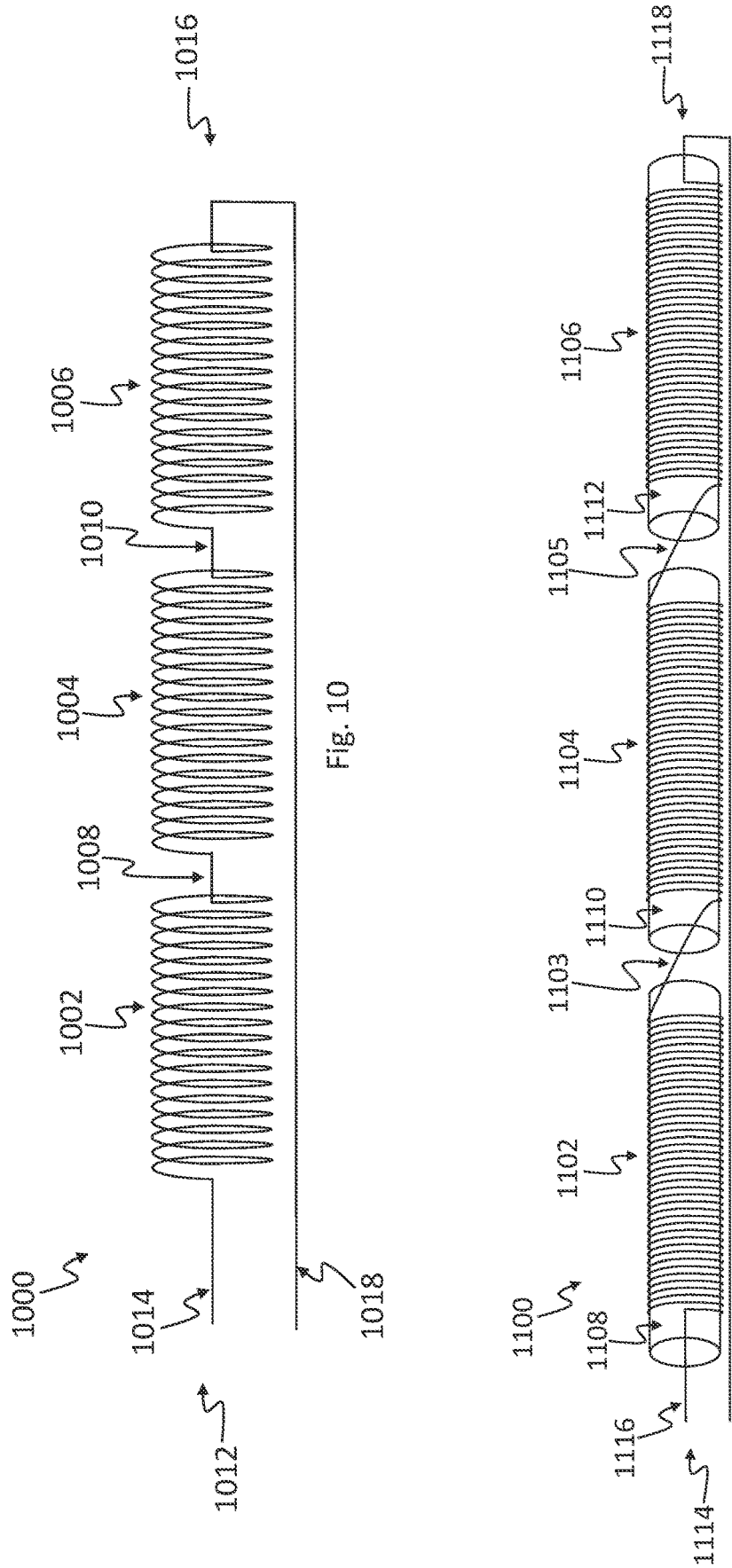

SENSOR CARRIER

CROSS-REFERENCE TO RELATED APPLICATIONS

This application is a continuation of International Patent Application No. PCT/EP2020/062086 filed on Apr. 30, 2020, which claims priority to U.S. Provisional Patent Application No. 62/842,025 filed on May 2, 2019, the disclosures of which are hereby incorporated by reference in their entirety.

The invention relates to an auxiliary instrument for insertion into vessels or lumens with small inner diameters.

Within the framework of minimally invasive surgery, today complex surgeries are performed inside a human body. Here, surgical instruments, such as endoscopes, are guided through a body opening into the human body to their target location inside the human body. To assist a surgeon in navigating surgical instruments inside a human body, optical, ultrasonic, or electromagnetic position detection systems can be used.

For example, electromagnetic position detection systems are known where a field generator generates an alternating electromagnetic field. A localization element formed by one or more coils then is arranged at a surgical instrument. Furthermore, a reference sensor also comprising coils is typically provided and arranged at a fixed position relative to a patient. The alternating electromagnetic field of the generator induces currents in the coils which depend on the orientation of the respective coil to the alternating electromagnetic field. If a surgical instrument equipped with such a localization element is moved in the generated alternating electromagnetic field, it is possible to determine position and orientation of the localization element relative to the stationary reference sensor based on the induced currents.

As described inter alia in DE 10 2011 119 073 A1, position and orientation of a localization element can then be continuously determined with an electromagnetic position detection system, e.g., during a surgical procedure. The current position of a surgical instrument with localization element registered in the position detection system can then be displayed on a monitor to a surgeon in tomographic, preoperatively obtained sectional images of a respective body part.

It is an object of the invention to develop an auxiliary instrument with a localization element whose position and orientation can be determined with an electromagnetic position detection system and a surgical instrument with such an auxiliary instrument.

With respect to the auxiliary instrument this object is achieved by an auxiliary instrument for insertion into vessels or for insertion into lumens with small inner diameters. The auxiliary instrument has a proximal end and a distal end and comprises at least one localization element whose position and orientation can be determined with an electromagnetic position detection system. The at least one localization element is arranged directly adjacent to the distal end of the auxiliary instrument or at least near the distal end of the auxiliary instrument. The at least one localization element is configured for capturing an alternating electromagnetic field. A distal end region of the auxiliary instrument extends from the distal end of the auxiliary instrument to a proximal end of the localization element and the localization element is arranged within this distal end region. In that part of the distal end region in which the at least one localization element is arranged, the auxiliary instrument has at least sectionwise a small bending stiffness of less than 10 Nmm$^2$. At least two lines are guided from the at least one localization element to the proximal end of the auxiliary instrument and are electrically conductively connected at least to the localization element. The at least one localization element has a length whose amount is at least ten times greater than the amount of an outer diameter of the at least one localization element.

The invention includes the recognition that such an auxiliary instrument in general is suitable for versatile use. Such an auxiliary instrument can, for example, be inserted into a lumen of another instrument, such as a surgical instrument or catheter, in order to obtain a surgical instrument or catheter whose position can be detected by means of an electromagnetic position detection system. The aforementioned instrument can also be used as an independent instrument in a surgical procedure. Accordingly, vessels or lumens with small inner diameters can be vessels or lumens of a human body or lumens of a surgical instrument. A corresponding lumen of a surgical instrument can, e.g. be configured in such a way that the auxiliary instrument according to the invention can be inserted into the lumen.

A particularly preferred application of the auxiliary instrument comprises inserting the auxiliary instrument into such lumens of a generally known instrument that were originally provided for a guidewire. Conventionally, for such instruments, a guidewire is first guided to its target location and then the instrument is advanced over the guidewire and guided along the guidewire to its target location. The guidewire advances in a provided lumen of the instrument, while the instrument slides along the guidewire.

If now instead of the guidewire an auxiliary instrument of the type described herein is inserted into the lumen of the instrument or catheter and the instrument or catheter is then used together with the auxiliary instrument, the position of the instrument itself can be determined using the position detection system and a guidewire is no longer required.

Instruments and implants that can be used with the auxiliary instrument described herein are, e.g., Jamshidi needles, taps, screwdrivers and pedicle screws that can be inserted with the screwdriver and, like the screwdriver, have a continuous central lumen for a guidewire.

By means of the auxiliary instrument described herein also balloon catheters or other catheters used for the dilation of body vessels can be turned into a catheter whose position can be determined by means of the position detection system during, e.g., surgery, in order to precisely determine the location of a dilatation.

Since the auxiliary instrument according to invention has at least one localization element which is configured for capturing an alternating electromagnetic field, the auxiliary instrument or a surgical instrument with an auxiliary instrument can be connected to an electromagnetic position detection system. Position and orientation of the at least one localization element can then be continuously determined with the respective electromagnetic position detection system and used to assist a surgeon during a surgical procedure. For example, the detected position and orientation of the at least one localization element can be used to display the position of the auxiliary instrument or of the surgical instrument with auxiliary instrument in tomographically obtained sectional images of a patient's body part. For example, the auxiliary instrument can be removably arranged in a Jamshidi needle so that position and orientation of the Jamshidi needle itself can be determined with a position detection system when penetrating a body part, such as a vertebral body of a spine. A surgeon can then follow the penetration of the Jamshidi needle into the vertebral body in tomographically obtained sectional images of the vertebral body virtually on a monitor. When placing the Jamshidi needle is completed, the auxiliary instrument can be removed and the lumen of the Jamshidi needle can be used for inserting another instrument.

The invention includes the further recognition that in a conventional localization element of a surgical instrument it is usually preferred that the amount of the length of the localization element is substantially equal to or at least not substantially greater than the amount of the outer diameter of the localization element. Generally, it is thus aspired to provide a localization element having a length as small as possible. Since the outer diameter of a common localization element having a small length must be comparatively large in order to provide a signal-to-noise ratio that is sufficient for determining position and orientation of the localization element, such a localization element is, in particular, not suitable for insertion into vessels or lumens with small inner diameters. Thus, already thin surgical instruments that, accordingly, have lumens with small inner diameters, cannot be connected to a position detection system with conventional localization elements.

It is advantageous that the auxiliary instrument according to the invention is so flexible, at least in sections, that it can adapt to a given shape of a vessel or lumen or that it can follow a course of a vessel or lumen with a small inner diameter. According to the invention this is achieved in that the auxiliary instrument, in particular in that part of the distal end region in which the at least one localization element is arranged, has at least in sections a small bending stiffness of less than 10 Nmm$^2$. The bending stiffness results from the product of the modulus of elasticity and the geometrical moment of inertia. The comparatively small bending stiffness of the localization element results, in particular, from a comparatively small geometrical moment of inertia. The comparatively small geometrical moment of inertia of the localization element results from the fact that the outer diameter of the localization element can be chosen comparatively small, since due to the length of the localization element being in magnitude at least ten times larger than its outer diameter, even with a small outer diameter a voltage signal with a signal-to-noise ratio sufficient for determining position and orientation can be generated.

The auxiliary instrument thus has at least one localization element with a comparatively small outer diameter and is therefore suitable for insertion into vessels or lumens with small inner diameters. In addition, the auxiliary instrument is, in particular in the distal end region, at least sectionwise flexible and can thus adapt to a predetermined shape or course of a vessel or lumen, although the at least one localization element has a comparatively large length of preferably more than 10 mm. At the same time, the auxiliary instrument can be connected to a position detection system in order to determine position and orientation of the at least one localization element, in particular during insertion into a vessel or lumen.

With respect to the surgical instrument, the abovementioned object is achieved by a surgical instrument having an externally accessible lumen in which an auxiliary instrument is removably arranged, the auxiliary instrument having at least the features of the auxiliary instrument according to the invention as described above.

A lumen of a surgical instrument can, for example, be tubular or in the form of a cannula and can have a comparatively small inner diameter, which is just dimensioned in such a way that an auxiliary instrument with an external diameter of less than, e.g., 0.5 mm can be inserted into the lumen accurately fitting to be, preferably, arranged immovably in the lumen.

The auxiliary instrument can be inserted into and removed from the lumen of the surgical instrument as a module if required. For example, the auxiliary instrument can be inserted into the lumen of the surgical instrument prior to surgery to connect the surgical instrument to a position detection system.

After positioning a first surgical instrument at a target site or also after a surgical procedure, the auxiliary instrument can be removed from the lumen of the first surgical instrument and then, if required, inserted into the lumen of another surgical instrument to connect this other surgical instrument to a position detection system.

Advantageously, the auxiliary instrument can be used for connecting surgical instruments that are configured in various ways as long as they have a lumen that is accessible from outside, into which the auxiliary instrument can be inserted to then be arranged inside.

Preferably, the surgical instrument is at least partially made of titanium or a chromium-nickel steel. Preferably, the surgical instrument is made of a paramagnetic material, such as paramagnetic steel or titanium, so that it can be used in an electromagnetic position detection system without affecting the generated electromagnetic field.

A surgical instrument with an auxiliary instrument can be a catheter, for example, in the lumen of which the auxiliary instrument is arranged. The catheter, for example a heart catheter, a suction catheter or a dialysis catheter, can then be connected to a position detection system using the auxiliary instrument. The catheter with auxiliary instrument can be used in a surgical procedure and can, e.g., be introduced into the bladder, stomach, intestine, vessels, but also into the ear or heart of a patient. During insertion, the position of the catheter with auxiliary instrument can be determined and position information can be made available to the surgeon. For example, the position of the catheter can be displayed in tomographically obtained sectional images to assist a surgeon in navigating the catheter inside a patient's body.

The catheter with auxiliary instrument can also be a balloon catheter equipped with a balloon which can be expanded, e.g., with compressed air or liquid. The balloon catheter with auxiliary instrument can be connected to a position detection system that can be used for determining the position of the balloon catheter during a surgical procedure. The balloon catheter can then be guided precisely to a target location in the human body in order to be expanded there. Such a balloon catheter with auxiliary instrument can be used, e.g., to dilate narrowed or blocked blood vessels, i.e., in angioplasty, or in urology to drain urine from the urinary bladder, or in orthopedics to treat vertebral fractures with the procedure of balloon kyphoplasty, or in pneumology to either dilate or to temporarily seal a bronchus, e.g., for surgery, or also in gynecology to reduce bleeding in a placenta accreta.

The auxiliary instrument can also be arranged in a lumen of a Jamshidi needle and used together with the Jamshidi needle. For example, with the Jamshidi needle with auxiliary instrument a bone marrow puncture can be performed, wherein the position of the Jamshidi needle can be determined with a position detection system while guiding the Jamshidi needle to a bone, e.g., to a vertebral body of a spine. The position of the Jamshidi needle can, e.g., be displayed in tomographically obtained sectional images such that a surgeon can virtually observe the penetration of the Jamshidi needle into a bone and guide the Jamshidi needle accordingly.

The auxiliary instrument can also be arranged in a lumen of a cutting tool, in particular of a threading tool, e.g., a thread cutter or a tap. For example, external threads for bone screws can be drilled with a tap. If a tap with an auxiliary instrument is connected to a position detection system, the position of the tap can be displayed in tomographically obtained sectional images to assist a surgeon in precisely positioning the tap above a bone and in assessing the progress of the drilling.

Like surgical screwdrivers, pedicle screws are cannulated so that the auxiliary instrument can be arranged in the screwdriver and pedicle screw in such a way that the distal end of the auxiliary instrument extends into the tip of the pedicle screw. Pedicle screw and screwdriver with the arranged auxiliary instrument can then be connected to a position detection system. The position of the pedicle screw, in particular, can then be displayed in tomographically obtained sectional images so that a surgeon can orientate himself on the tomographically obtained sectional images while placing the pedicle screw. In particular, a surgeon can precisely determine the location for screwing the pedicle screw into a bone and can control the penetration depth into the bone, e.g., into a vertebral body of a spine, based on the position of the pedicle screw in the tomographic sectional images. After placing the pedicle screw, the auxiliary instrument can be removed from the lumen of the screwdriver and pedicle screw and can be used for connecting a further surgical instrument. Pedicle screws or other screws with a lumen in which the auxiliary instrument is arranged can be used, for example, in the context of a spinal fusion, i.e., for screwing or stiffening vertebral bodies of a spine.

Further surgical instruments that can be equipped with the auxiliary instrument are those that commonly do not have a lumen, but that have been retrofitted with a lumen or that are manufactured with a lumen for such an auxiliary instrument ab initio. Such a surgical instrument can be a scalpel, a surgical saw, e.g. a bone saw, a bone file, a cautery, or tweezers. A surgical instrument with auxiliary instrument can then be connected to and used with a position detection system.

Since the auxiliary instrument has a localization element with a comparatively small outer diameter, the lumen of a surgical instrument can have a comparatively small inner diameter. Advantageously, a surgical instrument which has a lumen with a small inner diameter can itself be comparatively thin and can still be connected to a position detection system by means of an auxiliary instrument configured according to the invention. It is advantageous that an already flexibly designed surgical instrument remains flexible also with an arranged auxiliary instrument. Advantageously, a surgical instrument can also have several lumens with small inner diameters, into which, for example, differently designed auxiliary instruments can be inserted.

In the following, preferred embodiments of the auxiliary instrument according to the invention are described.

Preferably the localization element has an outer diameter of 0.5 mm or less, in particular, less than 0.3 mm. A localization element with an outer diameter of 0.5 mm; preferably, has a length of 5 mm or more. Accordingly, the length of a localization element having an outer diameter of 0.3 mm is at least 3 mm. It is preferred that the length of a localization element with an outer diameter of 0.5 mm or less is at least 10 mm. Even if at least one localization element of the auxiliary instrument has a length which is at least 10 mm, the auxiliary instrument in that part of the distal end region in which the at least one localization element is arranged has at least in sections a low bending stiffness of less than 10 Nmm².

The auxiliary instrument can also have at least two localization elements, each of which is electrically conductively connected to at least two electrical lines. Preferably, the at least two localization elements are electrically independent of each other and can be used for different functions. Preferably, the least two localization elements are both located within the distal end region which then extends from the proximal end of the localization element that is located closer to the proximal end of the auxiliary instrument to the distal end of the auxiliary instrument. In that part of the distal end region in which the at least two localization elements are arranged, the auxiliary instrument at least sectionwise has a low bending stiffness of less than 10 Nmm². Each of the localization elements can be formed by a single coil or by a coil arrangement formed by several electrically connected coils.

The localization element can be arranged spatially in the auxiliary instrument so that the distal end of at least one localization element forms the distal end of the auxiliary instrument. In this case, the length of the distal end region corresponds to the length of the localization element. However, if the localization element is arranged near the distal end of the auxiliary instrument and the localization element at a distance from the distal end of the auxiliary instrument, the length of the distal end region is the length of the localization element plus the distance to the distal end of the auxiliary instrument.

Preferably, the at least two electrical lines connected to a localization element are electrically insulated from each other and from the localization element.

The at least one localization element having a length that is at least ten times greater than the outer diameter of the localization element, preferably, has a total inductance that is between 2 mH and 4 mH. If the at least one localization element is formed by a single coil or a coil arrangement, preferably, the coil or the coil arrangement, respectively, has a total inductance of between 2 mH and 4 mH.

The alternating electromagnetic field typically generated by a field generator of a position detection system induces an electric current in the coil or coil arrangement forming the localization element according to the principle of electromagnetic induction, wherein the induced current depends on the orientation of the localization element within the alternating electromagnetic field. A voltage signal representing the voltage induced in the localization element can then be tapped via the lines electrically connected to the localization element. Since the localization element is preferably configured in such a way that the total inductance of the localization element is between 2 mH and 4 mH, a sufficiently high voltage can be induced in the localization element so that a tapped voltage signal, advantageously, has a signal-to-noise ratio so that position and orientation of the localization element in the alternating electromagnetic field can be determined comparatively reliably from the tapped voltage signal by the position detection system.

Preferably, the at least one localization element having a length that is at least ten times as large as the outer diameter of the localization element is configured in such a way that it has an electrical resistance that is between 70Ω and 100Ω. If a localization element is formed by a single coil or by several coils forming a coil arrangement, they have an electrical resistance that is between 70Ω and 100Ω.

The localization element with a length ten times greater than its outer diameter can be formed by a single coil having two coil ends. At each of the respective coil ends, the coil can be electrically conductively connected to a respective one of the electrical lines. A voltage signal tapped via the electrical lines then represents a voltage applied between the two coil ends. The coil, preferably, has an outer diameter of less than 0.5 mm, in particular, less than 0.3 mm, but more than 0.05 mm. Coils with an outer diameter of this magnitude are described inter alia in EP 0691663 A1. If the length l of a coil is large compared to the diameter A of a cross section of a coil, the inductance L results approximately reads $$L = \frac{\mu_0 \mu_r N^2 A}{l}$$

where $\mu_0$ is the magnetic field constant, $\mu_r$ the relative permeability, N the number of windings and A the cross-sectional area of the coil. In order to produce a coil with an inductance that is between 2 mH and 4 mH, the number of windings, the coil cross-section and the length of the coil should be chosen accordingly. In the case the coil is not wound around a coil core, the relative permeability is 1. The inductance of a coil can therefore be increased in that the coil is wound around a coil core that is made of a material with a high permeability. As a further boundary condition, the available thickness of a coil wire can be considered. The length of the coil results from the product of the number of windings and the wire thickness of the coil wire used. Typically, the length of a coil with an inductance between 2 mH and 4 mH is more than 10 mm. In particular, due to the preferred small outer diameter of the coil and the preferred small thickness of a coil wire to be used, in general, such a coil has a bending stiffness well below 10 Nmm². The bending stiffness is the product of the modulus of elasticity of the material used and the geometrical moment of inertia. The modulus of elasticity is a material constant. The bending stiffness, e.g., of a coil can thus be influenced, in particular, by changing the geometrical moment of inertia, i.e., by changing the cross-section geometry.

In the auxiliary instrument also at least two localization elements can be arranged, each formed by a single coil. Preferably, each of the coils is electrically conductively connected to at least two lines and electrically independent of the at least one other coil. Preferably, the lines are led from the respective coil to the proximal end of the auxiliary instrument. From each of the coils, a separate voltage signal can then be tapped. Since the coils provide independent voltage signals, the coils can be used for different functions.

In the auxiliary instrument, also at least two localization elements can be arranged in the distal end region, each of the localization elements being formed by a coil arrangement. It is also possible that an auxiliary instrument comprises a first localization element formed by a single coil and a further localization element formed by a coil arrangement.

At least one coil can be wound around a coil core. As already mentioned, the inductance of the coil can be increased by a coil core. A suitable material for a coil core is, e.g., soft iron which can have a permeability of up to 10,000. The coil core can be formed by a single piece which then preferably extends from at least one distal end of a coil to a proximal end of that coil. A coil core can also be formed by a plurality of lined up pieces that are movable relative to each other, the lined up pieces then preferably extending from at least one distal end of a coil to a proximal end of that coil. If a coil core is formed by several pieces that are movably lined up, it can be advantageous if the several pieces fit exactly into each other, e.g. like a ball joint. A coil core formed by several pieces can then adapt comparatively flexibly to a given shape of a vessel or lumen. Even if a coil core is made from a single piece, a coil core can have a bending stiffness of well below 10 Nmm² due to its small outer diameter. Generally, a coil core can be made of different materials. Preferably, however, the material used has a high permeability.

If a coil is wound around a coil core, a first coil end of the coil can be electrically conductively connected to a first of at least two lines and a second coil end of the coil can be electrically conductively connected to a distal end of the coil core. A proximal end of the coil core can then be electrically connected to a second of the at least two lines. The coil core then establishes an electrically conductive connection between the second coil end and the second line.

In an embodiment in which a coil is wound around a coil core and a first coil end of the coil is electrically conductively connected to a first of the at least two lines and a second coil end of the coil is electrically conductively connected to a distal end of the coil core, it can be advantageous if the coil core at its proximal end is not electrically conductively connected to a second of the at least two electrical lines but extends from the distal end of the coil to the proximal end of the auxiliary instrument. In this variant, the coil core can form one of at least two lines of the auxiliary instrument.

It can also be advantageous if the coil core extends beyond a distal end of a coil towards the proximal end of the auxiliary instrument, but not to the proximal end of the auxiliary instrument. At its proximal end, the coil core is then preferably electrically conductively connected to a second line of the at least two lines. However, in this embodiment the second of the at least two lines does not extend from a coil end to the proximal end of the auxiliary instrument, but from a proximal end of the coil core to the proximal end of the auxiliary instrument.

If the at least one localization element is formed by a single coil or a coil arrangement, at least one coil can also have at least one bending section within which the coil is comparatively flexible relative to the rest of that coil. For example, a bending section of a coil can be configured in such a way that in that section a number of windings per unit length of the coil is smaller than in the rest of the coil. Such a coil can also be wound around a coil core and, particularly in the bending section of the coil, has a bending stiffness of less than 10 Nmm².

At least one localization element can also be formed by a coil arrangement formed by several electrically interconnected coils. A coil arrangement is preferably formed by a number of coils connected in series. Preferably, a coil arrangement has at least one bending section located between two of the coils of the coil arrangement. The bending section of the coil arrangement located between two of the coils has a comparatively lower bending strength, in particular, compared to the coils of the coil arrangement. In particular, in that part of the auxiliary instrument in which a bending section of a coil arrangement is located, the auxiliary instrument has a bending stiffness of less than 10 Nmm². It is possible that between two bending sections or generally outside a bending section the auxiliary instrument has a bending stiffness that is greater than 10 Nmm².

A first coil arranged at a proximal end of a coil arrangement, preferably, is connected at its proximal coil end to a first of the at least two lines. A further coil arranged at a distal end of this coil arrangement, preferably, is electrically conductively connected at its distal coil end to a second of the at least two lines. Via the at least two electrical lines, a voltage signal can then be tapped at a coil arrangement which represents a voltage induced in the coil arrangement that is applied between the distal end of the coil arrangement and the proximal end of the coil arrangement.

If a coil arrangement is formed by a number of coils connected in series, the total inductance of the localization element results additively from the respective inductances of the individual coils of the coil arrangement. The individual coils of the coil arrangement can then, for example, be configured in such a way that they each have an inductance which is less than 2 mH. Bending of the coil arrangement then takes place essentially within a bending section, so that the coils themselves of the coil arrangement bend comparatively little under an exerted external force. The mechanical stress on the individual coils themselves can therefore be comparatively low. This applies in particular when compared to a localization element formed by a single coil having a length comparable to that of a coil arrangement and an inductance of between 2 mH and 4 mH at an outer diameter of less than 0.5 mm.

The coils of a coil arrangement and in particular each coil of a coil arrangement can be wound around a coil core, respectively, which then preferably extends from a proximal end of a respective coil to a distal end of that coil. Preferably, no coil core is provided in a bending section between two coils of a coil arrangement. The coil core allows the inductance of a single coil to be increased without increasing the bending stiffness in a bending section, so that the bending stiffness can be well below 10 $Nmm^2$. It is also possible that all coils of a coil arrangement are wound around a common coil core. The wire connections between the individual coils can then still form a bending section of the coil arrangement in which the coil arrangement bends preferentially under an exerted external force.

A coil arrangement can also be electrically conductively connected to at least a third line. Preferably, then a first coil arranged at a proximal end of the coil arrangement is electrically conductively connected at its proximal coil end to a first of the at least two lines and a further coil arranged at a distal end of the coil arrangement is electrically conductively connected at its distal coil end to a second of the at least two lines. The at least third line is then electrically conductively connected to the coil arrangement, preferably, in a section between the distal end and the proximal end of the coil arrangement. Preferably, an at least third line is electrically conductively connected to the coil arrangement in a bending section. A voltage signal can then be tapped between the at least third line and the first line and/or between the at least third line and the second line.

If a coil arrangement is electrically conductively connected to at least a third line, several voltage signals can be tapped.

For example, if the coil arrangement comprises two coils and the third line is electrically conductively connected to the coil arrangement in the bending section between the two coils, a voltage signal representing an induced voltage applied between the coil ends of the coil located between the first line and the at least third line can be tapped via the first line and the at least third line. Correspondingly, via the at least third line and the second line a voltage signal representing an induced voltage applied between the coil ends of the coil located between the at least third line and the second line can be tapped. Furthermore, via the first line and second line a voltage signal can be tapped that represents a voltage which is applied between the proximal end of the coil arrangement and the distal end of the coil arrangement and can thus be assigned to the coil arrangement itself.

The tapped voltage signals can then be evaluated separately and the extracted information can be combined to achieve increased reliability in determining the position and orientation of a localization element in the alternating electromagnetic field. It is also possible that certain information can only be extracted by comparing the tapped voltage signals in the course of the evaluation. For example, it is possible that by comparing the voltage signals, noise and an actual voltage signal can be distinguished from each other more reliably.

In particular, if the auxiliary instrument is intended to be inserted into a lumen of a surgical instrument in order to be arranged therein, it can be sufficient if the auxiliary instrument comprises at least one localization element and electrical lines electrically connected to the at least one localization element, only. However, it can be advantageous if the auxiliary instrument has additional mechanical stabilization. The at least one localization element and the at least two lines can, e.g., be enveloped by a tube. A tube then preferably has an outer diameter which is less than 0.6 mm but in particular larger than the outer diameter of the enveloped localization element. The auxiliary instrument can be given additional mechanical stability by means of a tube and at the same time the localization element and the lines can be protected from external influences.

A tube wall of a tube, preferably, has a thickness of 0.1 mm or less. Preferably, the tube is made of a material which leads to a bending stiffness of less than 10 $Nmm^2$. In particular, in that part of the distal end region of the auxiliary instrument in which a localization element is located the bending stiffness can also substantially be given by the bending stiffness of a tube of the auxiliary instrument. An auxiliary instrument with an external diameter of less than 0.6 mm specified by the tube is therefore still comparatively flexible, at least in sections, and thin and thus suitable for insertion into vessels or lumens which have a small internal diameter and also have a curved course or which can be difficult to access.

Preferably, a tube of the auxiliary instrument is made of a biocompatible material and/or an outer surface of the tube is coated with a biocompatible material. An auxiliary instrument with such a tube is particularly suitable for use in a surgical procedure inside a human body. Suitable biocompatible materials from which the tube of the auxiliary instrument can be made are for example polyurethane (PUR), polyethylene, silicone rubber or polyether ether ketone (PEEK). The auxiliary instrument with a tube made of one of these materials can advantageously be repeatedly sterilized, is biocompatible and radiolucent. It is therefore also possible to arrange X-ray markers, e.g., made of gold, in a tube of an auxiliary instrument, which are visible in, e.g., intraoperatively obtained X-ray images and can serve to determine the position and orientation of the auxiliary instrument during a surgical procedure. Thereby, electromagnetic position detection can be combined with fluoroscopic position detection. It can also be advantageous if the auxiliary instrument with a tube in which x-ray markers are placed is arranged in a lumen of a surgical instrument, so that the surgical instrument can be connected to an electromagnetic position detection system and be detected with a fluoroscopic position detection system.

At the proximal end of an auxiliary instrument a connection for electrical contacting can be arranged, which is preferably electrically conductively connected to the at least two leads. A connection can have a plug and/or a coupling. At a connection, an auxiliary instrument can be connected via a cable to a data processing device, such as a conventional computer, to transmit a tapped voltage signal to the data processing device. A data processing device is preferably part of a position detection system. A data processing device is preferably configured to evaluate a received voltage signal and to computationally determine position and orientation of a localization element.

The distance between the proximal end and the distal end of the auxiliary instrument is preferably between 10 cm and 200 cm, in particular, between 20 cm and 150 cm, preferably, between 30 cm and 100 cm. The auxiliary instrument can generally be manufactured in different lengths. Depending on the application, a shorter or longer length of the auxiliary instrument can be advantageous. It is possible that the auxiliary instrument has a length that is dimensioned so that a localization element extends over a comparatively large part of the length of the auxiliary instrument. If, for example, the auxiliary instrument has a length of 30 cm, a localization element can extend over a length of e.g. 3 cm and thus over one tenth of the length of the auxiliary instrument.

The auxiliary instrument can also have a proximal localization element in addition to the at least one localization element located in the distal end region. This proximal localization element is preferably arranged at a distance from the distal end region starting from the distal end region in the direction of the proximal end of the auxiliary instrument. The proximal localization element can be located immediately adjacent to the distal end region. Preferably, however, the distance between the proximal localization element and the distal end region is a few centimeters, e.g., between 5 cm and 15 cm. The proximal localization element is configured to capture an alternating electromagnetic field. Like the at least one localization element arranged in the distal end region, the proximal localization element can also be formed by a coil or a coil arrangement. In particular, the proximal localization element can be configured the same way as the localization element arranged in the distal end region of the auxiliary instrument.

Position and orientation of a localization element can be fully determined by determining six degrees of freedom, three translational and three rotational degrees of freedom. In particular, if a localization element is formed by a single coil, with this coil only five degrees of freedom can be determined. The sixth degree of freedom of the localization element, namely the rotation around the longitudinal axis of the coil, cannot be determined. However, if the auxiliary instrument has two localization elements, each formed by a single coil, that can be, e.g., a proximal localization element and a localization element arranged in the distal end region, it can be possible to reconstruct the sixth degree of freedom of each respective coil on the basis of the five degrees of freedom determined, respectively. This is particularly possible if the distal end region of the auxiliary instrument and thus the localization element arranged in this region is angled from the proximal localization element. The longitudinal axes of the two localization elements then do not point in the same direction, but are at an angle to each other.

Preferably, the auxiliary instrument having a proximal localization element in the region in which the proximal localization element is located has at least in sections a low bending stiffness of less than 10 Nmm$^2$. Advantageously, the auxiliary instrument then remains comparatively flexible even in the region in which the proximal localization element is arranged and can adapt to a rigid shape of the lumen when being inserted into a lumen. In particular, the auxiliary instrument can then also be arranged in such surgical instruments whose lumen has one or more curved sections. A surgical instrument that is already flexible itself, advantageously, remains flexible with an arranged auxiliary instrument having an additional proximal localization element also in that region in which the proximal localization element is arranged.

Preferably, the proximal localization element has a length with an amount that is at least ten times the amount of the outer diameter of the proximal localization element. Like the at least one localization element arranged in the distal end region, the proximal localization element can also have a comparatively small outer diameter and yet, due to its at least ten times greater length, be configured for outputting a voltage signal with a signal-to-noise ratio that is sufficient for determining position and orientation of the localization element. Since the outer diameter can be chosen comparatively small due to the at least ten times greater length, e.g., 0.5 mm or less, the auxiliary instrument can also have a low bending stiffness of less than 10 Nmm$^2$, at least in sections, in particular, also in that region in which the proximal localization element is arranged.

It is preferred that the proximal localization element is configured to have a total inductance of between 2 mH and 4 mH. Also in the proximal localization element a sufficiently high voltage can be induced so that a tapped voltage signal, advantageously, has such a signal-to-noise ratio that from the tapped voltage signal position and orientation of the proximal localization element in the alternating electromagnetic field can be determined comparatively reliably by the position detection system.

With the auxiliary instrument having an additional proximal localization element, on the one hand a method for reconstructing a bend in the distal end region of the auxiliary instrument can be performed in a particularly advantageous manner.

With the auxiliary instrument with an additional proximal localization element, on the other hand a method for reconstructing an outer shape of a surgical instrument, in the lumen of which the auxiliary instrument is arranged, can also be carried out particularly advantageously. In particular, the outer shape of a surgical instrument can be reconstructed in that region of the surgical instrument which is located between two localization elements of the auxiliary instrument arranged in the lumen of the surgical instrument.

Both, the method for reconstructing a bend of a distal end region of an auxiliary instrument and the method for reconstructing an outer shape of a surgical instrument, preferably, comprise the following steps:
  generating an alternating electromagnetic field,
  outputting a voltage signal with a localization element arranged in a distal end region which represents a voltage induced in the localization element,
  outputting a voltage signal with a proximal localization element that is arranged at a distance from the distal end region starting from the distal end region in the direction of the proximal end of the auxiliary instrument, wherein said voltage signal represents a voltage induced in the proximal localization element,
  determining position and orientation of the localization element arranged in the distal end region on basis of the voltage signal output from said localization element, and
  determining position and orientation of the proximal localization element that is arranged at a distance from the distal end region based on the voltage signal output from said proximal localization element.

In the method of reconstructing a bend of the distal end region of the auxiliary instrument, the bend is preferably reconstructed based on the determined position and orientation of the localization element arranged in the distal end region and the determined position and orientation of the proximal localization element arranged at a distance from the distal end region.

In the method of reconstructing an outer shape of a surgical instrument, the outer shape of the auxiliary instrument in the lumen of which the auxiliary instrument is arranged is reconstructed, preferably, on the basis of the determined position and orientation of the localization element arranged in the distal end region and the determined position and orientation of the proximal localization element arranged at a distance from the distal end region. The reconstruction of the outer shape of the surgical instrument relates in particular to the outer shape of the surgical instrument in the region lying between two localization elements. A reconstruction of the outer shape of the surgical instrument in this region is particularly facilitated in that position and orientation of both, the proximal localization element and the localization element arranged in the distal end region are determined independently of one another. For the reconstruction of the outer shape of the surgical instrument, further mechanical boundary conditions may have to be taken into account, such as the spatial relationship between the two localization elements and their arrangement within the auxiliary instrument.

The outer shape of the surgical instrument reconstructed with a suitable data processing device can be visually displayed on a monitor in various ways.

A possible application of the method for reconstructing an outer shape of a surgical instrument is, for example, in the area of minimally invasive ear, nose and throat (END surgery. For example, the outer shape of a balloon catheter can be reconstructed when being inserted into the human body. If the balloon is expanded, e.g., with compressed air or fluid, the shape of the expanded balloon can be reconstructed based on the determined position and orientation of the localization element located in the distal end region and the determined position and orientation of the proximal localization element arranged at a distance from the distal end region. The auxiliary instrument is then arranged in the balloon catheter in such a way that the balloon is located between the proximal localization element and the localization element of the auxiliary instrument arranged in the distal end region. The extent to which the balloon is expanded—i.e., for example, the approximate diameter of the expanded balloon—can be determined based on the pressure or amount of fluid (gas or liquid) introduced into the balloon to expand the balloon, so that there is no need for providing sensors to detect the expansion of the balloon. However, such sensors configured for sensing the balloon expansion can be provided.

The steps of "reconstructing a bend in the distal end region of the auxiliary instrument" and "reconstructing an outer shape of a surgical instrument" can also be part of the same method. In the same method, both, the bending of the distal end region of the auxiliary instrument as well as the outer shape of a surgical instrument can be reconstructed.

Figure 6:
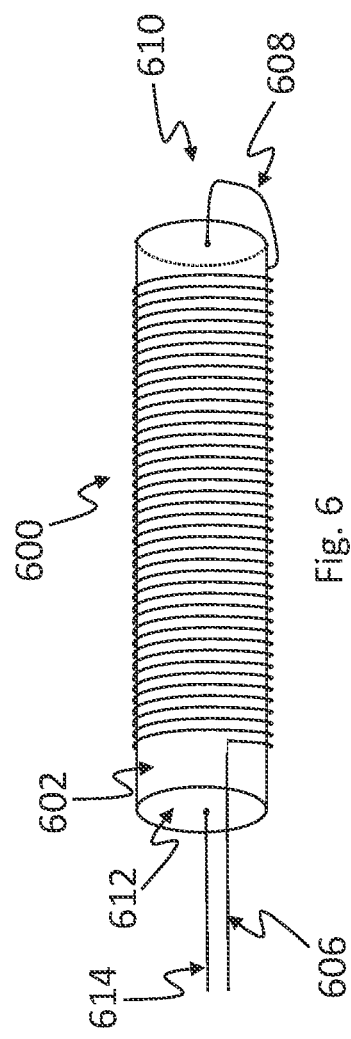
Figure 7:
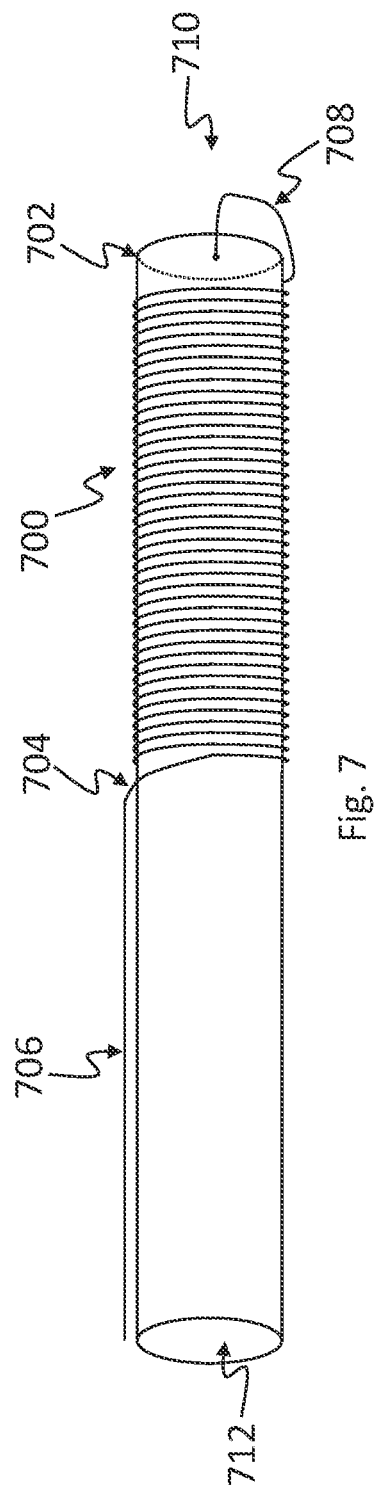
Figure 12:
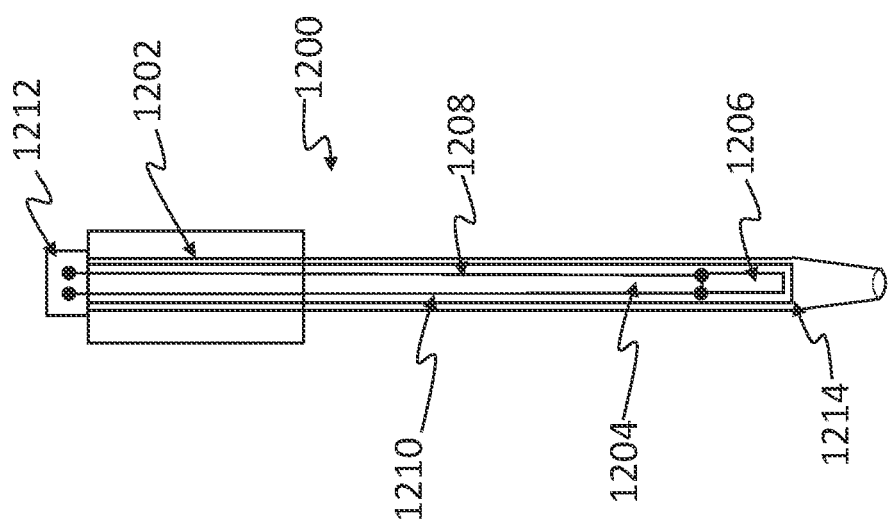

In the following, embodiments of the invention are described with reference to the figures. In the figures:

FIG. 1: shows a schematic and simplified illustration of an auxiliary instrument with a localization element and electrical lines, which are enveloped in a tube;

FIG. 2: shows a schematic and simplified illustration of a localization element which is formed by a coil that at each of its coil ends is electrically conductively connected to a respective electrical line;

FIG. 3: shows a schematic and simplified illustration of a localization element which is formed by a coil wound around a coil core;

FIG. 4: shows a schematic and simplified illustration of a coil core which is formed by several pieces that are movably stringed together;

FIG. 5: shows a schematic and simplified illustration of a single piece of a coil core, that can be formed by several of such pieces stringed together;

FIG. 6: shows a schematic and simplified illustration of a localization element formed by a coil wound around a coil core, wherein a first coil end of the coil being electrically conductively connected to a first electrical line, and a second coil end of the coil being electrically conductively connected to a distal end of the coil core and the proximal end of the coil core being electrically conductively connected to a second electrical line;

FIG. 7: shows a schematic and simplified illustration of a localization element formed by a coil wound around a coil core, wherein a first coil end of the coil being electrically conductively connected to a first electrical line, a second coil end of the coil being electrically conductively connected to the distal end of the coil core, and the coil core being a second electrical line;

FIG. 8: shows a schematic and simplified illustration of a localization element formed by a coil wound around a coil core, said coil having a bending section;

FIG. 9: shows a schematic and simplified illustration of a localization element formed by a coil arrangement comprising two coils connected in series, wherein a bending section being located between the coils, the coil arrangement being electrically conductively connected to a third electrical line in the bending section;

FIG. 10: shows a schematic and simplified illustration of a localization element formed by a coil arrangement, wherein the coil arrangement is formed by coils connected in series;

FIG. 11: shows a schematic and simplified illustration of a localization element formed by a coil arrangement, wherein the coil arrangement being formed by coils connected in series and each of the coils being wound around a respective coil core;

FIG. 12: shows a schematic illustration of a Jamshidi needle with an auxiliary instrument.

FIG. 1 shows a schematically depicted auxiliary instrument 100 with a localization element 102. The localization element 102 is electrically conductively connected to two electrical lines 104,106. The wires 104,106, are led from the localization element 102 to a proximal end 108 of the auxiliary instrument 100.

The localization element 102 and the lines 104,106 are surrounded by a tube 110, the tube extending from the proximal end 108 to a distal end 112 of the auxiliary instrument. The tube 110 is made of a biocompatible material so that the auxiliary instrument 100 is particularly suitable for use in a surgical procedure inside a human body. The tube 110 has an external diameter 114 of 0.5 mm and a tube wall of the tube has a thickness of 0.1 mm. The tube 110 extends beyond a distal end of the localization element 102 so that the distal end of the tube 110 forms the distal end 112 of the auxiliary instrument 100. Thus, the localization element 102 is arranged close to the distal end 112 of the auxiliary instrument 100 so that a distal end region 116 extends from the proximal end of the localization element 102 to the distal end of the tube 110. The localization element 102 is thus arranged within the distal end region 116 near the distal end 112 of the auxiliary instrument 100.

The localization element 102 has an outer diameter of 118, which is 0.4 mm and an inductance that is between 2 and 4 mH. The localization element 102 can, e.g., be formed by a coil as described with reference to FIG. 2, 3, 6, 7 or 8 or by a coil arrangement as described with reference to FIG. 9, 10 or 11. In particular then, if the localization element 102 is formed by a coil or a coil arrangement, the auxiliary instrument 100 in that part of the distal end region 116 in which the localization element 102 is arranged has at least in sections a low bending stiffness of less than 10 Nmm². A tube made of PEEK having the dimensions given herein typically has a bending stiffness of between 5 Nmm² and 10 Nmm² such that the bending stiffness of the auxiliary instrument 100 in that part of the distal end region 116 in which the localization element 102 is arranged, preferably, at least sectionwise corresponds substantially to the bending stiffness of the tube 110. Between the sections or outside the sections with a bending stiffness of less than 10 Nmm², the auxiliary instrument 100 can also have a bending stiffness of more than 10 Nmm², in particular, in that part of the distal end region 116 in which the localization element 102 is arranged. However, in a localization element 102 having a coil with an outer diameter of less than 0.5 mm and a length of more than 5 mm, preferably, more than 10 mm, it is possible that the bending stiffness of a used tube 110 is greater than the bending stiffness of the localization element 102. This can be particularly the case if a tube wall of the tube has a thickness that is in the order of the thickness of the outer diameter of a localization element or even significantly larger.

Due to the small outer diameter 118 of the localization element 102 and the small outer diameter 114 of the tube 110, the auxiliary instrument 100 itself is comparatively thin and particularly suitable for insertion into vessels or for insertion into lumens with small inner diameters, even if these are comparatively difficult to access. Here, it is advantageous that the auxiliary instrument 100, in particular in that part of the distal end region 116 in which the localization element 102 is arranged, is at least sectionwise flexible. The auxiliary instrument 100 thus has a comparatively small outer diameter and is nevertheless comparatively flexible, at least in sections, especially in the distal end region. The auxiliary instrument 100 can therefore be arranged in or inserted into vessels or lumens with small inner diameters and adapt flexibly to a shape given by the vessel or lumen. If, for example, a vessel of a human body has different branches, a branch can be selected by bending the auxiliary instrument in the distal end region and the remaining part of the auxiliary instrument can then follow the distal end of the auxiliary instrument into this branch.

The auxiliary instrument 100 with the localization element 102, whose position and orientation can be determined with an electromagnetic position detection system, can advantageously be connected to such a position detection system. With a position detection system position and orientation of the localization element 102 can then be determined while inserting the auxiliary instrument into a vessel. The information about position and orientation of the localization element 102 and, derived therefrom, position and orientation of the auxiliary instrument 100 can be made available to a user of the auxiliary instrument 100 during insertion into a vessel so that he can change or adapt a handling of the auxiliary instrument 100 on the basis of the information made available to him. For example, the position of the auxiliary instrument or of a surgical instrument with an arranged auxiliary instrument can be displayed in tomographically obtained sectional images of an object under examination during insertion into the human body on a monitor to a user. Thereby, advantageously, errors can be avoided and/or mechanical stress of human tissue can be reduced while inserting the auxiliary instrument into a vessel or while inserting the surgical instrument with auxiliary instrument into the human body. Because of determining position and orientation of the localization element a user can thus use an auxiliary instrument or a surgical instrument with auxiliary instrument in a more targeted and controlled manner. This is particularly important if a vessel has only a small inner diameter, is difficult to access and/or has a sensitive condition, e.g., has a sensitive outer wall and/or a surgical instrument has to be positioned precisely and/or penetration of a surgical instrument into sensitive tissue, e.g. bone tissue, shall be performed with improved control.

To use an auxiliary instrument 100 together with a position detection system, the auxiliary instrument 100 is typically connected via a cable (not shown) to a data processing device (not shown) of a position detection system so that a tapped voltage signal can be transmitted from the localization element 102 to a data processing device via the electrical lines 104, 106 and evaluated by the data processing device. The auxiliary instrument 100 can, for example, be connected via a plug connection (not shown) with a respective cable. For example, the auxiliary instrument 100 can have a connection (not shown) electrically conductively connected to electrical lines 104, 106 and located at the proximal end 108 of the auxiliary instrument 100.

The length of the auxiliary instrument 100 shown can be adapted to a planned use of the auxiliary instrument 100. Preferably, however, the auxiliary instrument 100 has a length of between 10 cm and 150 cm.

The auxiliary instrument 100 is also suitable to be inserted into a lumen of a surgical instrument (not shown). Since the auxiliary instrument 100 has a localization element 102 whose position and orientation can be determined with an electromagnetic position detection system, the auxiliary instrument 100 can be used to connect a surgical instrument to a position detection system. Preferably, such a surgical instrument has a lumen with a small inner diameter in which the auxiliary instrument 100 can be arranged. The lumen can have a small inner diameter that is just dimensioned to allow the auxiliary instrument to be immovably arranged in the lumen. Accordingly, the surgical instrument with a lumen itself can also be comparatively thin.

Since the auxiliary instrument 100 has a comparatively small outer diameter and, at the same time, despite the localization element, is comparatively flexible at least sectionwise, in particular in the distal end region, the auxiliary instrument can adapt to a given shape or course of a lumen of a surgical instrument and be immovably arranged in the lumen.

FIG. 2 shows a localization element formed by a coil 200. At each of the two coil ends 202, 204, the coil 200 is electrically conductively connected to a respective one of the electrical lines 206, 208 of an auxiliary instrument (not shown). The coil 200 is configured to capture an alternating electromagnetic field generated, e.g., by a field generator (not shown) of a position detection system. By changing the magnetic flux density, an electric field is generated in the coil 200 according to the principle of electromagnetic induction. Thereby, the current induced in the coil 200 depends on the orientation of the coil to the alternating electromagnetic field. Via the electrical lines 206, 208, a characteristic voltage signal can be tapped which represents an induced voltage applied between the coil ends 202, 204. The voltage signal can then be transmitted to and evaluated by a data processing device (not shown) of a position detection system. With the position detection system, position and orientation of the coil to the alternating electromagnetic field can be determined.

To ensure that a tapped voltage signal has a sufficiently good signal-to-noise ratio, the coil 200 is configured to have an inductance of between 2 mH and 4 mH. With a given outer diameter, the coil 200 must therefore have a corresponding number of windings and a length, such that an inductance in this range is achieved. An outer diameter of less than 0.5 mm typically results in a coil 200 having a length of more than 10 mm.

An auxiliary instrument can also have several localization elements, each formed by coils 200 as shown in FIG. 2. Preferably, each of the coils is then electrically conductively connected to at least two electrical lines, respectively. It is preferred that the several coils are not electrically connected to each other, so that an individual and, in particular, independent voltage signal can be tapped from each of the coils.

FIG. 3 shows a localization element formed by a coil 300 wound around a coil core 302. The coil 300 is preferably configured as described with reference to FIG. 2. Due to the comparatively small outer diameter of the coil 300 of less than 0.5 mm, the coil core 302 typically has a bending stiffness of significantly less than 10 Nmm$^2$ due to the low geometrical moment of inertia. Thus, if a localization element is formed by a coil 300 with coil core 302 as described herein and is surrounded by a tube (not shown) of an auxiliary instrument, it is possible that the relevant bending stiffness of the auxiliary instrument is determined by the bending stiffness of the tube.

If the coil core 302 is made of a material with high permeability, the inductance of the coil 300 can be significantly increased so that an inductance between 2 mH and 4 mH, for example, can already be achieved with a lower number of windings. When keeping the coil wire diameter constant, a lower number of windings results in a shorter length of coil 300. For example, coil core 302 can be made of soft iron which can have a permeability of up to 10,000. The coil core 302 shown is formed from a single piece and extends from a proximal end 304 of coil 300 to a distal end 306 of coil 300.

However, it can also be advantageous if a coil core is formed by several pieces that are movably stringed together. Such a coil core 400 is shown in FIG. 4. If such a coil core 400 is wound with a coil, this results in the synergetic effect of an increase in the inductance of the coil with simultaneously increased mobility of the pieces of the coil core 400 movably stringed together. The base area of the cylindrical pieces of the coil core 400 can be configured as a smooth surface as shown in FIG. 4. However, in order to avoid the forming of larger cavities during bending of such a coil core 400 formed by several pieces, it can be advantageous if a piece of such a coil core 400 has a base area with a different shape.

FIG. 5 shows a piece 500, which is one piece of a coil core formed by several pieces (not shown). This cylindrical piece of 500 does not have smooth base areas. Instead, one base area 502 has a concave curvature and the opposite base area 504 has a convex curvature. A coil core formed by such pieces of 500 can then be assembled in such a way that a respective concave curvature of one piece adjoins a convex curvature of an adjacent piece and these preferably fit exactly into one another. The two pieces can then move relative to each other similar to a joint. It is also possible that a piece (not shown) has two concave curved base areas and a coil core is formed from several of such pieces stringed together. The individual pieces can then roll against each other at their concave curved base areas in order to ensure comparatively good mobility of the coil core.

FIG. 6 shows a localization element formed by a coil 600 wound around a coil core 602. A first coil end 604 is electrically connected to a first line 606. A second coil end 608 is electrically connected to the distal end 610 of the coil core 602. The proximal end 612 of the coil core 602 is electrically conductively connected to a second line 614. The coil core 602 thus establishes an electrically conductive connection between the second coil end 608 of coil 600 and the second electrical line 614. The coil 600 has an outer diameter of less than 0.5 mm and a length preferably greater than 10 mm and, in particular, has a number of windings and a length chosen such that the coil 600 has an inductance of between 2 mH and 4 mH. Advantageously, the inductance of the coil 600 can be increased by a coil core formed by a material with high permeability, so that in turn a comparatively lower number of windings can be chosen in order to achieve an inductance of between 2 mH and 4 mH. In that the coil core 602 establishes an electrically conductive connection between the second coil end 608 and the second line 614, it is not necessary to guide the second line 614 past the coil 600 toward the distal end of the coil 600 to electrically connect the second line 614 to the second coil end 608 of the coil 600. An outer diameter of a localization element is then advantageously not increased by a line passing the coil 600.

FIG. 7 shows a localization element formed by a coil 700 wound around a coil core 702. At a first coil end 704, the coil 700 is electrically conductively connected to a first line 706. With a second coil end 708, the coil 700 is electrically conductively connected to the distal end 710 of the coil core 702. At its proximal end 712, the coil core extends beyond the proximal end of the coil and, in particular, to a proximal end of an auxiliary instrument (not shown). In contrast to the embodiment described with reference to FIG. 6, in which a coil core is electrically conductively connected at its proximal end to a second line, no further line is provided in the embodiment shown here. Instead, the coil core itself forms a second line that extends to a proximal end of an auxiliary instrument (not shown) and can be electrically conductively connected to a connection (not shown), particularly to connection contacts of a connection. It is possible that an auxiliary instrument can be given additional mechanical stability by a coil core extending to a proximal end of the auxiliary instrument.

FIG. 8 shows a coil 800 being wound around a coil core 802 and having a bending section 804. In the bending section 804 the coil 800 is comparatively flexible compared to the rest of the coil 800. The bending section 804 of coil 800 is configured in such a way that in this section a number of windings per unit length of coil 800 is smaller than in the rest of coil 800. Merely exemplary, in the embodiment shown, only two windings are provided in the bending section. This is intended to provide a better understanding of the bend section 804 of coil 800 de-scribed here, which, in a more realistic embodiment of a coil with a bend section can typically have several 100 windings in such a bend section, whereas the adjacent remaining parts of the coils can also have several 1000 windings. In contrast to a coil with a constant number of windings per unit length, the bending section 804 of the coil 800 shown here defines a section which, due to the lower number of windings per unit length, bends preferentially when force is exerted on the coil. The remaining parts of such a coil are therefore exposed to comparatively less mechanical stress. A single coil can also have several bending sections in which a number of windings per unit length of the coil is smaller than in the rest of the coil. Under the exertion of a force, a coil formed in this way then bends preferably at the several bending sections.

The coil 800 with bending section 804 shown in FIG. 8 is electrically conductively connected at a first coil end 806 with a first line 808 and at a second coil end 810 with a second line 812. However, it is also possible that at its second coil end 810 the coil 800 is electrically conductively connected to a proximal end of the coil core 802 as described with reference to FIG. 6. The distal end of the coil core 802 can then be electrically conductively connected to the second line 812 or can extend to a proximal end of an auxiliary instrument as described with reference to FIG. 7 to form the second electrical line itself. The coil core 802 in the embodiment shown is formed from a single piece, but can also be formed by several pieces movably stringed together as described with reference to FIG. 4 or 5.

FIG. 9 shows a coil arrangement 900 formed by two coils 902, 904 connected in series. The coil arrangement 900 has a bending section 906 located between the coils 902 and 904. Due to the simple wire connection of the two coils 902, 904, in this bending section 906 the coil arrangement 900 is comparatively flexible. The bending section 906 thus defines a section in which the coil arrangement 900 bends preferentially under the exertion of a force, so that the coils themselves change their shape comparatively minor under the exertion of a force.

The coils 902, 904 have a length, an outer diameter and a number of windings which are chosen in such a way that the respective inductances of the individual coils 902, 904 add up to a total inductance that is between 2 mH and 4 mH.

The coil 902 arranged at the proximal end 908 is electrically conductively connected at its proximal coil end to a first line 910. At its distal coil end 904, the coil 904 arranged at the distal end 912 of the coil arrangement 900 is electrically conductively connected to a second line 914. Via the first line 910 and the second line 914 a voltage signal can be tapped representing a voltage applied between the proximal end of coil 902 and the distal end of coil 904. The coil arrangement 900 is also electrically conductively connected to a third line 916. In the embodiment shown, the third electrical line 916 is electrically conductively connected to the coil arrangement 900 in the bending section 906. Thus, a further voltage signal can be tapped via the first line 910 and the third line 916, representing a voltage applied between the distal end of coil 902 and the proximal end of coil 902. Furthermore, a third voltage signal can be tapped via the third line 916 and the second line 914, representing a voltage applied between the distal end of coil 904 and the proximal end of coil 904.

Via the electrical lines 910, 914, 916 electrically conductively connected to the coil arrangement shown here, voltage signals assigned to the individual coils 902, 904 and a voltage signal assigned to the coil arrangement 900 can be tapped. All voltage signals can be transmitted to and evaluated by a data processing device (not shown). From the individual voltage signals or from the combination of the transmitted voltage signals position and orientation of the coil arrangement 900 of a localization element can then be determined. If no reliable determination of position and orientation is possible from a single voltage signal alone, e.g., due to a signal-to-noise ratio close to or less than one, by comparing the voltage signals it can nevertheless be possible to draw conclusions about position and orientation of the coil arrangement in an alternating electromagnetic field.

Only exemplary, the coil arrangement 900 is formed of only two coils 902, 904. However, for a coil arrangement to have a total inductance between 2 mH and 4 mH, it can be necessary, depending on the inductances of the individual coils, if a coil arrangement has more than two coils. Preferably, between these several coils there are bending sections. In the bending sections, a coil arrangement can be electrically conductively connected to a further line, respectively, so that voltage signals assigned to respective ones of the coils can be tapped via two of the respective lines. For example, a voltage signal can be tapped via a fourth and a fifth line, the fourth line being electrically conductively connected to the coil arrangement in a bend section adjacent to a proximal end of a respective coil, and the fifth line being electrically conductively connected to the coil arrangement in a bend section adjacent to a distal end of said respective coil. It is also possible, that further lines are electrically conductively connected to a coil arrangement in such a way that a voltage signal can be tapped which represents a voltage applied between the proximal end of a first coil and a distal end of an adjacent coil and can thus be assigned to these several coils.

FIG. 10 shows a coil arrangement 1000 formed by three coils 1002, 1004, 1006 connected in series. Between each two of the coils 1002, 1004, 1006 there is a bending section 1008, 1010. Due to the simple wire connections, in this bending section 1008, 1010 the coil arrangement 1000 is comparatively flexible compared to areas where coils 1002, 1004, 1006 are arranged. Only exemplarily, here, the number of coils 1002, 1004, 1006 is chosen to be three. In embodiments not shown here, a coil arrangement can also be formed by two coils connected in series or by more than three coils connected in series. Since the inductances of the individual coils 1002, 1004, 1006 add up to a total inductance of between 2 mH and 4 mH of the coil arrangement 1000, it is advantageous to increase the number of coils 1002, 1004, 1006 to such an extent that the coil arrangement 1000 has a total inductance in this range. In particular, if the coils 1002, 1004, 1006 have a comparatively small number of windings and, accordingly, a comparatively small inductance, a comparatively large number of such coils 1002, 1004, 1006 can be necessary for a coil arrangement to have a total inductance of between 2 mH and 4 mH.

At its proximal coil end, the coil 1002 arranged at a proximal end 1012 of the coil arrangement 1000 is electrically conductively connected to a first line 1014. The coil 1006 arranged at the distal end 1016 of the coil arrangement 1000 is electrically conductively connected with its distal coil end to a second line 1018, so that via the first line 1014 and the second line 1018 a voltage signal can be tapped which represents a voltage applied between the proximal coil end 1012 and the distal coil end 1016 of the coil arrangement 1000. The coil arrangement 1000 shown here can be electrically conductively connected to other lines, in particular, in the bending sections 1008, 1010, as described with reference to FIG. 9. If the coil arrangement 1000 in the bending sections 1008, 1010 is electrically conductively connected to a further electrical line, respectively, respective further voltage signals can be tapped. These additional voltage signals can, e.g., be assigned to a respective coil 1002, 1004, 1006 of coil arrangement 1000.

FIG. 11 shows a coil arrangement 1100 formed by three coils 1102, 1104, 1106 connected in series. Between two of the coils 1102, 1104, 1106, respectively, there is a bending section 1103, 1105 in which the coil arrangement is comparatively flexible. Each of the coils 1102, 1104, 1106 is wound around a respective coil core 1108, 1110, 1112. Each of the coil cores 1108, 1110, 1112 extends from a proximal end of a respective coil 1102, 1104, 1106 to a distal end of said respective coil 1102, 1104, 1106. Because each of the coil cores 1108, 1110, 1112 extends from a proximal end to a distal end of a respective coil 1102, 1104, 1106, only, in particular, no coil cores 1108, 1110, 1112 are arranged in the bending sections 1103, 1105. The bending stiffness of a bending section 1103, 1105 is therefore not influenced by a coil core 1108, 1110, 1112, but solely defined by the wire connection between the coils 1102, 1104, 1106.

Coil 1102 that is arranged at a proximal end of coil arrangement 1114, is electrically conductively connected at its proximal coil end to a first line 1116. Coil 1106, arranged at the distal end 1118 of coil arrangement 1000, is electrically conductively connected at its distal coil end to a second line 1120. As described with reference to FIG. 9, the coil arrangement 1100 can be electrically conductively connected, especially in the bending sections 1103, 1105, with a further line (not shown), respectively. Via the first line 1116 and the second line 1118 a voltage signal assigned to the coil arrangement 1100 can be tapped and via optional further electrical lines further voltage signals, e.g., assigned to the individual coils 1102, 1104, 1106 can be tapped.

Coils 1102, 1104, 1106 each can also have a further bending section that is realized in that in this section the number of windings per unit length is smaller than in the rest of a corresponding coil 1102, 1104, 1106, as described with reference to FIG. 8. Thereby, in addition to the bending sections 1103, 1105 already provided between two of the coils 1102, 1104, 1106, further bending sections that are configured as described with reference to FIG. 8 can be implemented, in which the coil arrangement 1100 bends preferentially under the exertion of a force.

FIG. 12 shows a schematically illustrated Jamshidi needle 1200 as an example of a surgical instrument with auxiliary instrument. In a 1202 lumen of the Jamshidi needle 1200 an auxiliary instrument 1204 is arranged. The auxiliary instrument 1204 comprises a localization element 1206 which can be formed by a coil as described with reference to FIG. 2, 3, 6, 7 or 8 or by a coil arrangement as described with reference to FIG. 9, 10 or 11. The localization element 1206 is connected to two lines 1208, 1210, which are led from the localization element 1206 to a connection 1212 of the auxiliary instrument 1204 for electrical contacting with a complementary connection, e.g. of a cable (not shown). The cable can be connected at its other end to a position detection system which is also not shown.

Localization element 1206 and lines 1208, 1210 are surrounded by a tube 1214, which gives the auxiliary instrument 1204 additional stability. Via the lines 1208, 1210 and the cable, a voltage signal representing a voltage induced in the localization element 1206 can then be transmitted to and evaluated by the position detection system for determining position and orientation of the localization element 1206. From the determined position and orientation of the localization element 1206, position and orientation of the Jamshidi needle 1200 can then be calculated. For example, the localization element 1206 can be calibrated to the tip of the Jamshidi needle 1200 prior to surgery with the Jamshidi needle 1200.

The invention claimed is:

1. An auxiliary instrument for determining a position of a second device, the auxiliary instrument comprising a proximal end, a distal end region, and an outer diameter, said auxiliary instrument further comprising a first localization element configured to have an electrical resistance between 70 ohms and 100 ohms and a second localization element whose positions and orientations can be determined with an electromagnetic position detection system, wherein the first localization element is arranged within the distal end region and comprises a first coil, and the second localization element is arranged within the distal end region and comprises a second coil, wherein said auxiliary instrument is configured to insert into a lumen of the second device, said lumen of the second device having an inner diameter larger than the outer diameter of the auxiliary instrument, and wherein, during insertion, the position of said second device is determinable.

2. The auxiliary instrument of claim 1, wherein the distal end region comprises a bending stiffness of less than 10 Nmm$^2$.

3. The auxiliary instrument of claim 1, wherein the first localization element is configured to have a total inductance between 2 mH and 4 mH.

4. The auxiliary instrument of claim 1, wherein the first coil has two coil ends and an outer diameter of 0.5 millimeters or less.

5. The auxiliary instrument of claim 1, wherein the first and second coils are electrically independent and each of the coils is electrically conductively connected to at least two electrical lines, the electrical lines being led from a respective coil to the proximal end of the auxiliary instrument.

6. The auxiliary instrument of claim 1, wherein the first coil is wound around a coil core being formed of a single piece extending at least from a distal end of the first coil to a proximal end of the first coil, or around the coil core being formed of several pieces movably stringed together, the coil core extending at least from a distal end of the first coil to a proximal end of the first coil.

7. The auxiliary instrument of claim 6, wherein a first coil end of the first coil is electrically conductively connected to a first of at least two electrical lines, and a second coil end of the first coil is electrically conductively connected to a distal end of the coil core, and a proximal end of the coil core is electrically conductively connected to a second of the at least two electrical lines so that the coil core establishes an electrically conductive connection between the second coil end and the second electrical line.

8. The auxiliary instrument of claim 6, wherein a first coil end of the first coil is electrically conductively connected to a first of at least two electrical lines, and a second coil end of the first coil is electrically conductively connected to a distal end of the coil core, and wherein the coil core extends from a distal end of the first coil to the proximal end of the auxiliary instrument and is one of the at least two electrical lines of the auxiliary instrument.

9. The auxiliary instrument of claim 1, wherein the first coil comprises a bending section that is less rigid than a remaining part of the coil.

10. The auxiliary instrument of claim 1, wherein the first localization element comprises a coil arrangement comprising a number of coils connected in series, the coil arrangement having at least one bending section which is located between two of the coils of the coil arrangement.

11. The auxiliary instrument of claim 10, wherein each coil of the coil arrangement is wound around a respective coil core extending from a proximal end of a respective coil to a distal end of that coil such that no coil core is arranged in a bending section between two of the coils.

12. The auxiliary instrument of claim 1, wherein the first and second localization elements is surrounded by a tube.

13. The auxiliary instrument of claim 12, wherein the tube is coated with a biocompatible material.

14. The auxiliary instrument of claim 1, wherein a connection for an electrical contact is arranged at the proximal end of the auxiliary instrument.

15. The auxiliary instrument of claim 1, wherein a distance between the proximal end and the distal end of the auxiliary instrument is between 10 cm and 150 cm.

16. The auxiliary instrument of claim 1, further comprising a proximal localization element at the proximal end of the auxiliary instrument.

17. The auxiliary instrument of claim 1, wherein the proximal end comprises a bending stiffness of less than 10 $Nmm^2$.

18. The auxiliary instrument of claim 16, wherein the proximal localization element is configured to have a total inductance between 2 mH and 4 mH.

19. The auxiliary instrument of claim 1, wherein the second device comprises a catheter.

20. The auxiliary instrument of claim 19, wherein the catheter comprises a balloon catheter.

21. The auxiliary instrument of claim 19, wherein the catheter comprises an angioplasty catheter, a urinary catheter, a gastrointestinal catheter, or a dialysis catheter.

22. The auxiliary instrument of claim 1, wherein the second device comprises a bone screw, a pedicle screw, or a Jamshidi needle.

23. An auxiliary instrument for determining a position of a second device, the auxiliary instrument comprising a proximal end, a distal end region, and an outer diameter, said auxiliary instrument further comprising a first localization element and a second localization element whose positions and orientations can be determined with an electromagnetic position detection system, wherein the first localization element is arranged within the distal end region and comprises a coil arrangement comprising a number of coils connected in series, the coil arrangement having at least one bending section which is located between two of the coils of the coil arrangement, and the second localization element is arranged within the distal end region and comprises a second coil, wherein said auxiliary instrument is configured to insert into a lumen of the second device, said lumen of the second device having an inner diameter larger than the outer diameter of the auxiliary instrument, and wherein, during insertion, the position of said second device is determinable.

24. The auxiliary instrument of claim 23, wherein each coil of the coil arrangement is wound around a respective coil core extending from a proximal end of a respective coil to a distal end of that coil such that no coil core is arranged in a bending section between two of the coils.

25. The auxiliary instrument of claim 23, wherein the first and second localization elements is surrounded by a tube.

26. The auxiliary instrument of claim 25, wherein the tube is coated with a biocompatible material.

27. The auxiliary instrument of claim 23, wherein a connection for an electrical contact is arranged at the proximal end of the auxiliary instrument.

28. The auxiliary instrument of claim 23, wherein a distance between the proximal end and the distal end of the auxiliary instrument is between 10 cm and 150 cm.

29. The auxiliary instrument of claim 23, further comprising a proximal localization element at the proximal end of the auxiliary instrument.

30. The auxiliary instrument of claim 23, wherein the proximal end comprises a bending stiffness of less than 10 $Nmm^2$.

31. The auxiliary instrument of claim 29, wherein the proximal localization element is configured to have a total inductance between 2 mH and 4 mH.

32. The auxiliary instrument of claim 23, wherein the second device comprises a catheter.

33. The auxiliary instrument of claim 32, wherein the catheter comprises a balloon catheter.

34. The auxiliary instrument of claim 32, wherein the catheter comprises an angioplasty catheter, a urinary catheter, a gastrointestinal catheter, or a dialysis catheter.

35. The auxiliary instrument of claim 23, wherein the second device comprises a bone screw, a pedicle screw, or a Jamshidi needle.

36. The auxiliary instrument of claim 23, wherein the first localization element is configured to have an electrical resistance between 70 ohms and 100 ohms.

* * * * *